(12) United States Patent
Hirakawa et al.

(10) Patent No.: US 6,961,122 B2
(45) Date of Patent: Nov. 1, 2005

(54) MEASUREMENT CHAMBER WITH ADJUSTABLE OPTICAL WINDOW

(75) Inventors: Seiichi Hirakawa, Kyoto (JP); Tetsu Kochi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 212 days.

(21) Appl. No.: 10/425,759

(22) Filed: Apr. 29, 2003

(65) Prior Publication Data
US 2004/0001200 A1    Jan. 1, 2004

(30) Foreign Application Priority Data
Apr. 30, 2002    (JP)    .............................. 2002-127875

(51) Int. Cl.⁷ ............................................ G01N 21/01
(52) U.S. Cl. ...................................................... 356/244
(58) Field of Search ........................ 356/244, 335–343, 356/36–50; 250/363.02–363.04, 366

(56) References Cited

U.S. PATENT DOCUMENTS

| | | | |
|---|---|---|---|
| 5,094,099 A | | 3/1992 | Ross |
| 5,777,331 A | * | 7/1998 | Muehllehner .......... 250/363.03 |
| 5,982,847 A | * | 11/1999 | Nelson ......................... 378/47 |

FOREIGN PATENT DOCUMENTS

| | | |
|---|---|---|
| DE | 199 62 198 | 12/1999 |
| WO | WO 03/014794 | 2/2003 |

OTHER PUBLICATIONS

Collins et al. "Effects of processing conditions on the growth of nanocrystalline diamond thin films: real time spectroscopic ellipsometry studies" Diamond and Related Materials, Elsevier Science Publishers, Amsterdam, NL, vol. 6, no. 1, 1997, pp. 55-80.

* cited by examiner

*Primary Examiner*—Tu T. Nguyen

(57) ABSTRACT

A measurement chamber assembly for removing the effects of optical aberrations when a sample is irridated from light through optical windows it is provided. A housing member can support and receive a sample. One or more optical windows for viewing the sample and more particularly for permitting an irridation of light to contact the sample and to be transmitted out of the sample chamber as provided. A mounting unit is movably connected to the housing member so that the optical window or windows can be moved relative to the housing member to vary and angle the optical axis for viewing the sample. The optical windows can be positioned orthogonal to the optical axis to minimize optical aberrations.

13 Claims, 3 Drawing Sheets

MEASUREMENT CHAMBER WITH ADJUSTABLE OPTICAL WINDOW

BACKGROUND OF THE INVENTION

1. Field of the Invention

The present invention relates to a measurement chamber that permits an application of light for measuring a property of a sample, and more particularly, a measurement chamber with an optical window that permits an adjustment of the optical window while maintaining the integrity of the measurement chamber so that it can be used in spectroscopic measurements.

2. Description of Related Art

Numerous different instruments utilize an illumination of a sample with radiation, including light in the visible, ultraviolet and infrared ranges where the light interacts with the sample to provide a characteristic that can be appropriately measured to determine the properties of the sample. Various forms of spectroscopic measuring devices such as optical interferometers and ellipsometers position a test sample within a sample chamber having an optical window or windows that isolate the sample from exterior influences such as atmospheric pressure and temperatures.

FIG. 6 discloses a prior art schematic view of a conventional testing instrument with an optical window 66. A sample chamber 61 is usually maintained at a low pressure or vacuum state and/or at a low temperature, and the optical window 66 isolates its interior with the sample 63 from the exterior ambient conditions. Light 68 is disclosed as entering into the sample chamber 61 through the optical window 66 for interacting with the sample 63. The light 69 that has been influenced by the sample is also outputted via the optical window 66 to a detector not shown.

The angle of entrance and exit of the light 68 is inclined with regards to the optical window 66, and the measurement results cannot be performed for the same point on the sample 63 due to the influences of chromatic aberration.

In the case of performing a spectral ellipsometric measurement by using a low temperature cryostat, there is also a need for varying the angle of light entering into the sample chamber to define a measurement point on the surface of the sample. If the light enters at an angle as it transmits through an optical window, there is a potential problem in that the optical path or optical axis can be varied depending on the wave length because the optical window is fixed. As a result, errors in the measurement can be realized.

SUMMARY OF THE INVENTION

The present invention provides an improved measurement sample chamber with an optical window movably connected to the measurement sample chamber by an optical window supporting member so that it can be adjustable relative to the light extending through the optical window to a desired measurement point on the sample. The optical window can be arranged to be orthogonal to the light transmission to minimize optical aberrations. The housing member for receiving the sample can be provided with a mounting unit that is movably connected to the housing member and which in turn mounts the optical window for viewing the sample along an optical axis.

The mounting unit permits the optical window to move relative to the housing member to vary an angle of the optical axis for viewing the sample. For example, the optical axis can be inclined relative to the sample while the optical window can be positioned to be orthogonal to the optical axis to minimize any optical aberrations such as chromatic aberration. The present invention can be employed in spectroscopic measurement devices that permit the application of light to a sample and then detecting light from the sample to measure properties of the light, characteristic of the sample. A mounting unit is movably connected to the spectrophotometric device for viewing the sample, and the optical window is connected to this mounting unit and movable with the mounting unit.

The present invention also includes a method of correcting optical errors that can occur with a sample chamber for receiving a sample. The sample chamber has a first optical window for transmitting the light, and the method includes aligning a light source to contact the sample and moving the first optical window relative to the sample chamber to a position to minimize any influence of optical errors caused by the optical window when the light is transmitted through the optical window. The sample chamber can include a second optical window movably mounted to the sample chamber for transmitting light from the sample and includes the further steps of moving the second optical window relative to the sample chamber to minimize any influence of optical errors caused by the second optical window when light is transmitted through the second optical window.

Various forms of optical window supporting units can be provided such as a metallic flexible tube or a bellows that can seal the optical window to the sample chamber while permitting relative movement of the optical window. The optical window supporting member can further be an optical window cylinder or tube for supporting the optical window. A receiving cylinder can be formed at one side of the sample chamber for receiving the optical window cylinder, and a sealed portion can be provided between the optical window cylinder and the receiving cylinder.

An alternative mounting arrangement can include an optical window supporting member formed on an optical window cylinder for supporting the optical window with a guide portion or slot receiving a circular arc-shaped slide plate provided on the optical window cylinder. The side plate and guide portion is capable of hermetically sealing the sample chamber while still permitting a sliding movement of the side plate for relative adjustment of the optical window.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1:
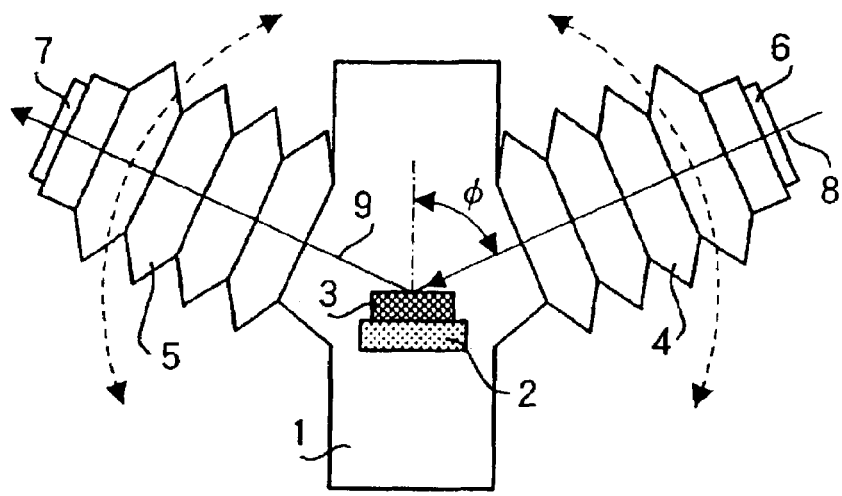
FIG. 1 is a partial cross-sectional schematic view illustrating a first example of a measurement chamber with an optical window of the present invention.

Various embodiments of the present invention will be described with reference to the drawings. FIG. 1 shows a schematic view illustrating an example of a measurement chamber with optical window. A sample 3 to be measured is placed on a sample stand 2 in a sample chamber 1. The sample chamber 1 is provided with a support mounting unit 4 for supporting a first optical window 6 for incident light and a support mounting unit 5 for supporting a second optical window 7 for emitting light. The terminology "first" and "second" are for purposes of illustration and are not limiting since a first window can also receive emitting light by itself or receive both incident and emitting light depending on the instrument. Each of the mounting units 4 and 5 can be formed of a metallic bellow hermetically fixed to the sample chamber 1 and thus they have flexibility for moving the optical windows. The support members 4 and 5 can maintain their deformed states to maintain the desired position of the optical windows.

Optical windows 6 and 7 are hermetically fixed to one end of the flexible support mounting units 4 and 5, respectively. The flexible support mounting units 4 and 5 can move in the directions shown by the arrows in FIG. 1 and also can move into and out of the shown plane. When incident light 8 enters the center of the sample 3 along an optical axis with an incident angle φ, an adjustment can be performed so that the surface of the optical window 6 is orthogonal to the incident light 8.

Similarly, an emitting light 9, subject to the influence of the sample 3, such as interference and polarization enters an unillustrated detection head. In this case also, the metallic bellow constituting the support mounting unit 5 is adjusted so that the light 9 is orthogonal to the surface of the second optical window 7 by the same manner as the above-described first optical window 6.

Figure 2:
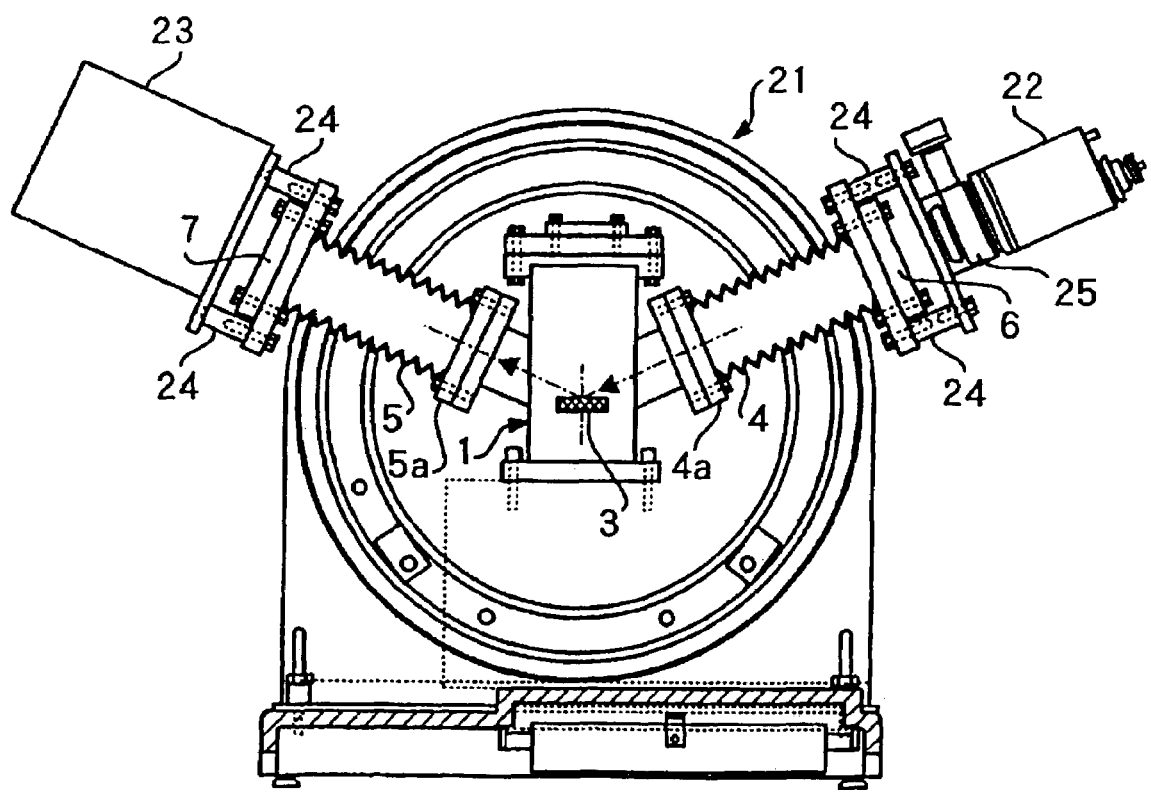
FIG. 2 is a side view of the measurement chamber and optical window of FIG. 1 combined in a goniometer.

FIG. 2 is a view illustrating a detailed example of the first embodiment used with a goniometer. The sample chamber 1 is used with a goniometer 21. A measurement point on the sample 3, placed within the sample chamber 1, serves as the target center for the optical axis of the detector and source of light. The above-described support mounting unit 4 formed of a metallic bellow is hermetically fixed via a flange 4a to the sample chamber 1. Similarly, the support mounting unit 5 is also hermetically fixed via a flange 5a to the sample chamber 1. The optical window 6 is fixed to the support mounting unit 4, and the optical window 7 is fixed to the support mounting unit 5, respectively. Fixed to a frame for supporting the optical window 6 is an optical head (optical light source) 22 via a plurality of poles 24 (four poles in this example) and an optical head fixing member 25. An optical head (light receiving detector) mounting plate 23 is fixed via poles 24 to a frame for supporting the optical window 7. For measurement, an incident angle may be varied within a certain range, for example, within ±10 degrees.

Figure 3:
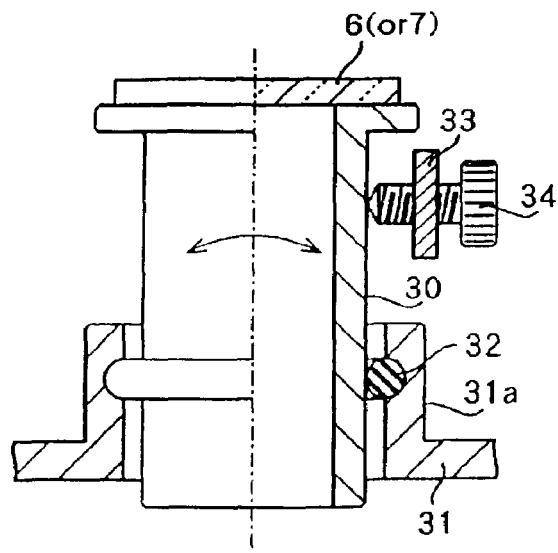
FIG. 3 is a partial side cross-sectional view of a second embodiment of the present invention showing an optical cylinder supporting unit.

FIG. 3 is a schematic view illustrating another example of an optical window supporting member used for the device of the present invention. An unillustrated sample is placed within a sample chamber 31. The sample chamber 31 is provided with support members for supporting an optical window 6 for incident light and an optical window 7 for emitting light. Because the support members or mounting units have substantially the same structure, only one support member will be described.

The sample chamber 31 is provided with a receptacle cylinder 31a for receiving a viewing tube or cylinder. An optical window supporting cylinder 30 is inserted into the cylinder 31a via a seal member (O-ring) 32 constituting a seal portion and supported thereby. The optical windows 6 or 7 are hermetically fixed to the respective optical window supporting or mounting unit 30. An adjustment screw 34 is provided in an arm 33, and the angle of the optical window supporter cylinder 30 can be adjusted within a range of deformation of the seal member (O-ring) 32 while still maintaining a hermetic sealing, that is the mounting unit 30 can be tilted relative to the sample 3 about the seal member 32.

Figure 4:
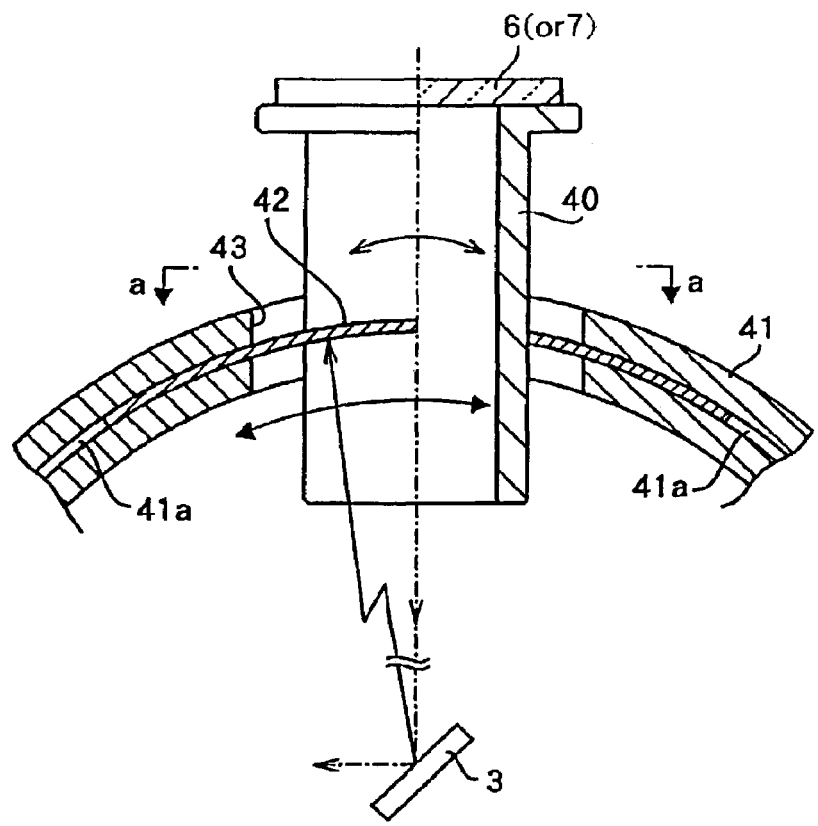
FIG. 4 is a partial schematic cross-sectional view of a third embodiment of an optical window supporting member in a directional orthogonal to the optical axis of the supporting member.
Figure 5:
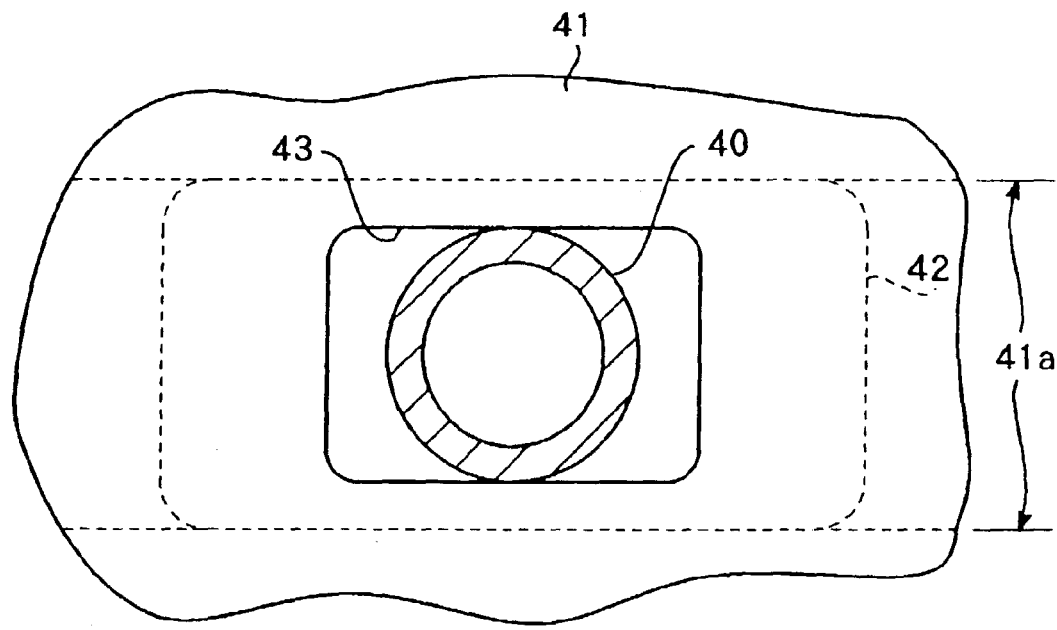
FIG. 5 is a cross-sectional view taken along the arrows aa of the embodiment shown in FIG. 3 seen from a direction parallel to the optical axis.
Figure 6:
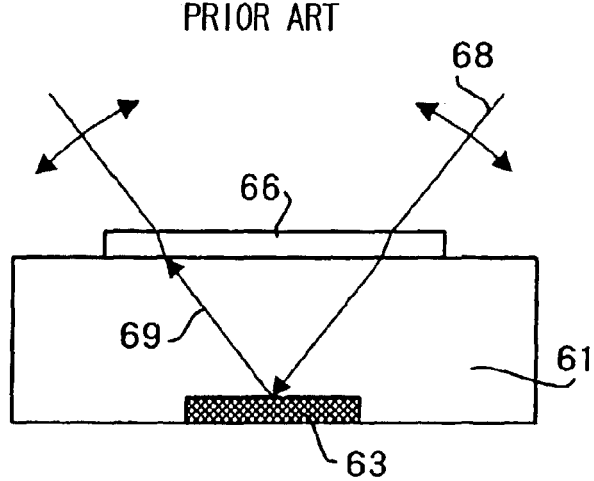
FIG. 6 is a schematic view of a conventional device with an optical window.

FIG. 4 is a schematic view illustrating yet another example of an optical window mounting unit that can be used in the device of the present invention, as seen from a direction orthogonal to the optical axis of the mounting unit. FIG. 5 is a cross-sectional view along lines (a—a) of the example seen from a direction parallel to the optical axis.

A sample chamber opening 43 is provided in a sample chamber housing 41. The optical window supporting unit has an optical window supporting cylinder 40 for supporting the optical window 6 or 7. The optical window supporting cylinder 40 is provided with a slide plate 42 for hermetically guiding within a guide opening or slot 41a with respect to the sample chamber opening 43. The slide plate 42 has a circular arc-shaped configuration. The guide opening 41a is a space which is provided within the walls of the sample chamber housing 41 and in which the circular arc-shaped slide plate 42 is guided in a circular arc manner.

In order to maintain hermetic sealing, viscous seal material such as grease or the like can be used in the guide opening 41a. The optical window supporting cylinder 40 is slid in a circular arc manner and thus is able to maintain, if desired, the surfaces of the optical windows 6 or 7 orthogonal to an optical path.

In accordance with a measurement chamber having an optical window of the present invention, adjustment is possible so that an optical path along an optical axis is orthogonal to the optical window. Accordingly, the beam position on a sample can be maintained at the same point even if an incident angle for the sample is required. Even if spectral measurement is performed while varying an incident angle, influences of chromatic aberration are not exerted and the beam position on a sample can be always maintained at the same point.

The sample chamber of the present invention is especially effective in spectral ellipsometric measurements and spectral reflection measurements for a sample under a low temperature condition or a vacuum condition. Namely, angle variable measurement becomes possible upon a sample under low temperatures. Because a window of a low temperature cryostat (vacuum chamber) is adjusted so as to be orthogonal to an optical path, influences of chromatic aberration are reduced in spectral measurement and thus the beam position on a sample is always maintained at the same point.

Various types of modifications may be performed upon the embodiments described in detail within the scope of the present invention. The present invention may be widely utilized in other measurements including reflectance measurement as well as spectral ellipsometric measurement. Further, the present invention may be utilized in the case that a beam is converged and in the case that an optical window is formed with a lens configuration so as to maintain a desired wavefront. In this case, adjustment is performed so that a plane parallel to an optical axis is orthogonal to an optical path.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A measurement chamber assembly comprising:
   a housing member for receiving a sample;
   a first optical window for viewing the sample along an optical axis;
   a second optical window;
   a first mounting unit movably connected to the housing member and the first optical window to enable the first optical window to move relative to the housing member to vary an angle of the optical axis for viewing the sample; and
   a second mounting unit moveably connected to the housing member, wherein the first optical window and the second optical window are positioned orthogonal to the optical axis to minimize refraction of light along the optical axis.

2. The measurement chamber assembly of claim 1 wherein the first optical window is offset from the housing member.

3. The measurement chamber assembly of claim 1 wherein the first mounting unit includes a bellows member.

4. The measurement chamber assembly of claim 1 wherein the first mounting unit includes a viewing tube.

5. The measurement chamber assembly of claim 1 wherein the housing member includes a guide portion and the first mounting unit includes a slide plate mountable within a guide opening.

6. The measurement chamber assembly of claim 1 wherein the housing member, first optical window and first mounting unit are sealed to enable a below atmospheric pressure to be applied to the sample.

7. The measurement chamber assembly of claim 1 wherein both the first and second mounting units include flexible members to permit relative movement to the housing member.

8. In a spectroscopic measurement device for applying light to a sample and detecting the light from the sample, the improvement comprising;
   a first mounting unit movably connected to the spectroscopic measurement device for viewing the sample;
   a first optical window connected to the first mounting unit and movable with the first mounting unit;
   a second mounting unit connected to the spectrosconic measurement device; and
   a second optical window connected to the second mounting unit and movable with the second mounting unit wherein an optical axis extends from the first optical window to the sample and from the sample to the second optical window and the first and second optical windows are positioned orthogonal to the optical axis to minimize refraction effects on the transmitted light.

9. The device of claim 8 wherein the first mounting unit includes a bellows member.

10. The device of claim 8 wherein the first mounting unit includes a viewing tube.

11. The device of claim 8 wherein the spectroscopic measurement device includes a guide portion and the first mounting unit includes a slide plate mountable within a guide opening.

12. The device of claim 8 wherein the spectroscopic measurement device, first optical window and first mounting unit are sealed to enable a below atmospheric pressure to be applied to the sample.

13. A method of correcting optical errors in a spectroscopic measurement device having a sample chamber for receiving a sample, the sample chamber having a first optical window and a second optical window for transmitting light comprising the steps of:
   aligning a light source to contact the sample;
   moving the first optical window relative to the sample chamber to a position to minimize any influences of optical errors caused by the first optical window on the light transmitted through the first optical; and
   moving the second optical window relative to the sample chamber to minimize any influence of optical errors caused by the second optical window on light transmitted through the second optical window, wherein an optical axis extends from the first optical window to the sample and from the sample to the second optical window and the moving steps position the first and second optical windows orthogonal to the optical axis to minimize refraction effects on the transmitted light.

* * * * *